(12) United States Patent
Brück et al.

(10) Patent No.: US 6,522,408 B1
(45) Date of Patent: Feb. 18, 2003

(54) PROCEDURE FOR THE CONTROLLED PRODUCTION OR MODIFICATION OF POLYMERIC PRODUCTS BY MEANS OF IR-ATR SPECTROSCOPY

(75) Inventors: Dieter Brück, Köln (DE); Udo Wolf, Kempen (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/246,179

(22) Filed: Feb. 4, 1999

(30) Foreign Application Priority Data

Feb. 12, 1998 (DE) .......................... 198 05 612

(51) Int. Cl.⁷ .................. C08F 2/00; C08F 8/00; C08F 8/04; C08F 236/12; G01N 21/35
(52) U.S. Cl. .................. 356/436; 525/329.3; 525/338; 525/339
(58) Field of Search .............. 525/329.3, 338, 525/339; 356/436

(56) References Cited

U.S. PATENT DOCUMENTS

| | | | | |
|---|---|---|---|---|
| 4,835,389 A | * | 5/1989 | Doyle | 356/436 |
| 5,051,551 A | * | 9/1991 | Doyle | 250/341.2 |
| 5,170,056 A | * | 12/1992 | Berard et al. | 250/341.2 |
| 5,754,722 A | * | 5/1998 | Melling | 356/436 |
| 5,773,825 A | * | 6/1998 | Doyle | 250/339.11 |
| 5,835,231 A | * | 11/1998 | Pipino | 356/436 |
| 5,926,269 A | * | 7/1999 | Von Der Eltz et al. | 356/300 |

FOREIGN PATENT DOCUMENTS

| | | | |
|---|---|---|---|
| CA | 2245182 | | 2/1999 |
| DE | 4333560 | * | 4/1995 |
| DE | 4414975 | * | 11/1995 |

OTHER PUBLICATIONS

Ullman's Encyclopedia of Industrial Chemistry, vol. A23, pp. 322–324 (1993).*
Catalysis Today 49 (month unavailable) 1999, pp. 411–418, Udo Wolf et al, Application Of infrared ATR spectroscopy to in situ reaction monitoring.
Applied Systems Inc., ReactIR™ Reaction Analysis Systems, (date unavailable).

* cited by examiner

*Primary Examiner*—D. R. Wilson
(74) *Attorney, Agent, or Firm*—Joseph C. Gil; Lyndanne M. Whalen; Jennifer R. Seng

(57) ABSTRACT

This invention relates to a procedure for the controlled production or for the modification of polymeric products using IR-ATR spectroscopy, wherein the case of a polymerization reaction the extinction is determined of the characteristic IR absorption bands for the monomer used and the resulting polymeric product or in the case of a polymer modification the characteristic IR absorption bands of the starting material used and of the modified polymeric product are determined, the degree of conversion or the degree of modification is calculated from the absorption bands, and when the desired degree of conversion or the desired degree of modification is reached the reaction is stopped by suitable measures. By means of the procedure, which is described according to the invention, it is possible to carry out polymerization reactions or the modification of polymeric products to the desired degree of conversion or degree of modification by means of IR-ATR spectroscopy, without high technical expenditure and under accurately controlled conditions.

5 Claims, No Drawings

PROCEDURE FOR THE CONTROLLED PRODUCTION OR MODIFICATION OF POLYMERIC PRODUCTS BY MEANS OF IR-ATR SPECTROSCOPY

The present invention relates to a procedure for the controlled production or for the modification of polymeric products using IR-ATR spectroscopy.

It is known, for example, that partially hydrogenated acrylonitrile-butadiene rubbers (HNBRs) can be produced using Raman spectroscopy. By employing Raman spectroscopy during the production of HNBR rubbers it is possible to effect controlled hydrogenation of the acrylonitrile-butadiene rubbers which are used. In this connection, we refer to the German Patent Application with the Application Number 19736310.5.

One disadvantage of Raman spectroscopy is the high level of technical expenditure which is associated therewith, since a powerful laser is necessary for the excitation of the Raman spectrum. It is therefore desirable to be able to use an alternative method of measurement for the controlled production or modification of polymeric products. Infrared—Attenuated Total Reflection (IR-ATR) spectroscopy is a known technique of analyzing a liquid media with an optical probe. IR-ATR spectroscopy is an example of a possible alternative to Raman spectroscopy. This method of measurement has hitherto been used preferentially for the analysis of low-viscosity media. For the analysis of media of higher viscosity it has hitherto been necessary to make the measurement by means of a bypass which is mounted on the reactor in order to ensure sufficiently rapid mass transfer at the surface of the ATR crystal.

It must therefore be deemed to be surprising that it is possible, by means of IR-ATR spectroscopy and by using the procedure described in more detail below, to effect production or modification of polymeric products under accurately controlled conditions so as to achieve the desired degree of conversion or degree of modification.

The present invention therefore relates to a procedure for the controlled production or for the modification of polymeric products using IR-ATR spectroscopy, which is characterised in that a) in the case of a polymer reaction the extinctions are determined of the characteristic IR absorption bands for the monomers used and of the resulting polymeric product or b) in the case of a polymer modification the characteristic IR absorption bands are determined of the starting material used and of the modified polymeric product, the degree of conversion or the degree of modification is calculated from the absorption bands, and when the desired degree of conversion or the desired degree of modification is reached the reaction is stopped by suitable measures, wherein the IR-ATR measurement is made directly, by means of an immersion probe, in an agitated reactor at short time intervals at maximum viscosities of the reactor contents of 10,000 Pas, preferably 10 to 1000 Pas, and at velocities of flow within the range from 0.01 to 10 m/sec, as measured at the location of the IR-ATR probe, and the degree of conversion or degree of modification is calculated as follows:

$$M(t) = 100 - \frac{A(t)}{A(t_0)} \cdot 100[\%]; \quad 1.$$

$$U(t) = 100 - \frac{A(t)}{A(t_0)} \cdot 100[\%]; \quad 2.$$

wherein $M(t)$=the degree of modification at time t $U(t)$=the degree of conversion at time t $A(t)$=the extinction of a characteristic absorption band of the monomer used or of the starting material at time t $A(t_0)$=the extinction of the characteristic absorption band of the monomer used or of the starting material at time $t_0$ (start of the reaction).

In the present invention, a characteristic absorption band is to be understood as an absorption band which is present for the monomer used or for the starting material to be modified, which absorption band decreases during the reaction or modification and is no longer present in the polymeric product obtained or in the modified polymeric product.

The desired degree of conversion or the desired degree of modification depends on the respective polymer reaction or modification reaction. The degree of conversion for a polymer reaction should usually be at least 70%, preferably at least 80%, particularly at least 90%; the degree of modification can—as mentioned—be between 5 and 95% depending on the requirements.

The viscosities of the reactor contents during the IR-ATR measurement are most preferably 10 to 200 Pas. The velocities of flow are preferably 0.01 to 10, most preferably 0.1 to 2 m/sec.

In the procedure according to the invention, it is advisable to measure the IR-ATR spectra at time intervals of about 1 second to 1 hour, preferably of 10 seconds to 10 minutes, particularly of 30 seconds to 5 minutes.

By means of the procedure according to the invention, it is possible, for example, to control Polymer reactions, i.e. Polymerisation reactions which proceed by a radical mechanism, condensation Polymerisations and addition polymerisations. For example, the procedure according to the invention is suitable and is Preferably used for the controlled production of polyesters, polyamides, polycarbonates, polystyrene and polystyrene copolymers, and olefines, as well as synthetic rubbers, provided that the production of the polymers is effected in a homogeneous melt or in solution within said viscosity range, Particularly for the production of polyethylene terephthalate, polybutylene terephthalate, polymethyl methacrylate, polyester- or polyurethane-based lacquer resins, polyamide 6, polyamide 6.6, bisphenol A polycarbonate, polystyrene, acrylonitrile-styrene copolymers, acrylonitrile-butadiene-styrene copolymers, polyethylene, polypropylene, polybutadiene, styrene-butadiene copolymers, polychloroprene, acrylonitrile-butadiene copolymers, ethylene-vinyl acetate copolymers, ethylene-propylene copolymers and isobutylene copolymers (butyl rubber).

Examples of modification reactions for polymeric products include hydrogenation reactions of unsaturated polymers, and the functionalisation of polymeric products, such as halogenation and carboxylation reactions.

The hydrogenation reaction of NBR rubbers should be emphasised as a particular example of the modification of polymeric products.

Therefore, the procedure according to the invention also relates to the controlled modification of nitrile rubbers (NBR rubbers) using IR-ATR spectroscopy, which is characterised in that the characteristic IR absorption bands of the NBR used and of the hydrogenated NBR are determined, the degree of modification is calculated from the absorption bands and when the desired degree of modification is reached the reaction is stopped by suitable measures, wherein the IR-ATR measurement is made directly, by means of an immersion probe, in an agitated reactor at time intervals from 10 seconds to 20 minutes at viscosities of the reactor contents from 1 to 100 Pas, preferably from 1 to 50 Pas, and at velocities of flow within the range from 0.1 to 10 m/sec, preferably from 1 to 8 m/sec, as measured at the location of the IR-ATR probe, and the degree of modification is calculated from the formula given above for the degree of modification.

The hydrogenation of NBR is effected here in the usual manner, by the batch-wise hydrogenation of NBR solutions in an agitated pressure autoclave with hydrogen. The polymer concentration in the solution to be hydrogenated is about 15% by weight. The homogeneous and heterogeneous catalysts which are used for hydrogenation, as well as the reaction conditions for hydrogenation, are described in greater detail in Ullmann's Encyclopedia of Industrial Chemistry of 1993.

Examples of ATR immersion probes which are suitable for the procedure according to the invention for the controlled production or modification of polymeric products by means of IR-ATR spectroscopy include the ATR immersion probe of Type DPR 111 manufactured by Axiom Analytical Inc., 18103 Sky Park South, Irvine, Calif. 92714, USA, which is commercially available, or similarly constructed ATR immersion probes of sufficient pressure- and temperature-resistance. The IR-ATR measurement is made in an agitated reactor at the aforementioned velocities of flow and viscosities of the reactor contents.

Filter photometers, diverse spectrometers or Fourier transform (FT)-IR spectrometers which are available on the market and which produce the IR spectrum by means of an interferometer can be used for measuring the IR-ATR spectra. FT-IR spectrometers are preferably used in the procedure according to the invention, because IR spectra can thereby be measured with a particularly good signal/noise ratio.

To record the IR-ATR spectrum of the reactor contents, the continuous spectrum of the FT-IR spectrometers is conducted to the ATR crystal located in the reactor, and after passing through the crystal is conveyed to the detector situated outside the reactor. If the IR spectrometer is placed at a location further from the reactor, suitable fibre-optic waveguides are used for the transport of the IR radiation. However, the fibre-optic waveguides which are currently available for the medium IR spectral range are only capable of transporting the IR signal over distances of a few meters, due to considerable signal losses.

When employing the IR-ATR technique, the amount of radiation energy transported into the reactor is so small that it is not capable of constituting a potential source of ignition, and is not capable of initiating unwanted secondary reactions. The claimed measuring procedure thus possesses a high level of inherent safety.

The IR-ATR spectra, which, in order to improve the signal/noise ratio, are accumulated over a defined time interval using a Fourier transform infrared (FT-IR) spectrometer (e.g. 200 scans with a spectral resolution of 4 $cm^{-1}$) are then evaluated over the spectral range from 4000 to 800 $cm^{-1}$.

During the modification (hydrogenation) according to the invention of NBR rubbers, the IR-ATR spectra of NBRs exhibit the following characteristic signals for the C=C double bonds of the butadiene units: A(970) for 1,4-trans C=C at about 970 $cm^{-1}$, A(730) for 1,4-cis C=C at about 730 $cm^{-1}$ and A(920) for 1,2-vinyl C=C at about 920 $cm^{-1}$. The CN grouping (nitrile group) gives an IR signal A(2237) at about 2237 $cm^{-1}$.

The procedure according to the invention is explained in greater detail below with reference to the hydrogenation of NBR rubbers.

EXAMPLES

The following individual steps were undertaken in order to determine the current degree of hydrogenation during the hydrogenation of NBR rubbers in solution in chlorobenzene by means of the IR-ATR method:

1. Determining the content of 1,4-trans C=C double bonds DB(1,4-trans) of the NBR product which was used for hydrogenation, before hydrogenation was effected by means of a classical laboratory method.
2. Recording the IR-ATR spectrum $A_0(v)$ at time t=0 before hydrogenation under the relevant hydrogenation conditions (temperature, pressure, concentration). The intensity spectrum determined using a non-wetted ATR crystal was employed as the background spectrum.
3. Determining the extinction of the nitrile group $A_0(2237)$ at about 2237 $cm^{-1}$ (basis line: 2260–2210 $cm^{-1}$)
4. Subtraction of an IR-ATR spectrum, which was stored in the computer of the spectrometer and which was recorded under the same conditions (pressure, temperature, concentrations, ATR crystal, spectral resolution), of a completely hydrogenated product solution, with a variable, multiplicative factor for the stored spectrum, so that the absorption of the differential spectrum was minimised at 903 $cm^{-1}$ (chlorobenzene absorption).
5. Determining the extinction of the 1,4-trans C=C double bonds $A_0(970)$ at 970 $cm^{-1}$ with a basis line between 1043 and 950 $cm^{-1}$.
6. Calculating the ratio $Q_0=A_0(970)/A_0(2237)$.
7. Recording the IR-ATR spectrum $A_t(v)$ at time t of the hydrogenation. The intensity spectrum determined using a non-wetted ATR crystal was employed as the background spectrum.
8. Determining the extinction of the nitrile group $A_t(2237)$ at about 2237 $cm^{-1}$ (basis line: 2260–2210 $cm^{-1}$)
9. Subtraction of an IR-ATR spectrum, which was stored in the computer of the spectrometer and which was recorded under the same conditions (pressure, temperature, concentrations), of a completely hydrogenated product solution, with a variable, multiplicative factor for the stored spectrum, so that the absorption of the differential spectrum was minimised at 903 $cm^{-1}$.
10. Determining the extinction of the 1,4-trans C=C double bonds $A_t(970)$ at 970 $cm^{-1}$ with a basis line between 1043 and 950 $cm^{-1}$.
11. Calculating the ratio $Q_t=A_t(970)/A_t(2237)$.
12. Calculating the ratio $RD_t(1,4\text{-trans})=Q_t/Q_0*DB(1,4\text{-trans})$.

A solution of 225 g NBR (with an acrylonitrile content, which was not determined exactly, of about 40%, and a butadiene content of about 60%, comprising 85.5% of 1,4 trans, 7.3% of 1,4 cis and 7.2% of 1,2-vinyl butadiene units), 2.25 g triphenyl-phosphine, 0.675 g of a rhodium catalyst and 1275 g chlorobenzene were introduced under nitrogen into a 5 liter autoclave fitted with an ATR immersion probe and with a multistage impulse counter-current agitator. The solution was subsequently flushed three times with nitrogen at a speed of rotation of 280 min$^{-1}$ and was depressurised to normal pressure each time.

A modified probe supplied by Axiom Analytical Inc., 18103 Sky Park South, Irvine, Calif. 92714, USA, Type DPR 111, with a cylindrical ATR crystal of ZnSe, diameter of the ATR crystal ⅛ inch, length 1.55 inch, sealing material: Kalrez, length of the ATR probe: 52 cm, was used as the ATR probe. The pressure-resistant barrier described in DE 4414975 was integrated in the ATR immersion probe. The IR-ATR spectra were recorded using a Nicolet 510-FT-IR spectrometer comprising an MCT detector cooled by liquid nitrogen.

The reaction solution was first heated to the reaction temperature of 135° C. The IR-ATR method described above was then employed. After carrying out steps 1–6, the following value was obtained for the ratio of the IR-ATR extinctions $Q_0=A_0(970)/A_0(2237)$ of the starting material at 135° C.: $Q_0=7.88$.

The autoclave was then charged with hydrogen at a total pressure of 35 bar. At the same time, an automated spectrum measurement and evaluation program was started for steps 7–12. This program enabled the hydrogenation at time t to be followed on-line, and enabled the instantaneous residual double bond content $(Rd)_t$ to be displayed on the screen of the computer which was connected.

The time requirement for each spectrum was about 2 minutes, with the exception of 200 scans at a resolution of 4 cm$^{-1}$ each time. After a time of hydrogenation of 6.5 hours, the ratio of the IR-ATR extinctions $Q_t=A_t(970)/I_t(2237)=0.993$. A 1,4-trans residual double bond content corresponding to $$RD_t(1,4\text{-trans})=[0.993/7.88]*85.5\%=10.8\%$$

was thus calculated from steps 11–12.

Since it is known that the 1,4-cis and 1,2-vinyl double bonds of NBRs are hydrogenated preferentially compared with the 1,4-trans double bonds, the degree of modification was accordingly 89.2%. The reaction was stopped at this value by depressurising to normal pressure.

We claim:
1. A process for the controlled production of polymeric products and/or modification of polymeric products comprising
   a) determining characteristic IR absorption bands for the starting material and the desired product,
   b) determining the absorbance of the characteristic IR absorption bands from a),
   c) immersing an IR-ATR probe in an agitated reactor having contents with a maximum viscosity of 10,000 Pas and flow velocity of from 0.01 to 10 m/sec at the probe location,
   d) measuring absorption directly by means of the IR-ATR probe at short time intervals during the production or modification reaction,
   e) calculating degree of conversion and/or degree of modification of the reactor contents using one of the following equations:

$$M(t) = 100 - \frac{A(t)}{A(t_0)} \cdot 100(\%)$$

or $$U(t) = 100 - \frac{A(t)}{A(t_0)} \cdot 100(\%)$$

in which
M(t)=degree of modification;
U(t)=degree of conversion;
A(t)=absorbance of the characteristic absorption band of the starting material at time t, and
$A(t_0)$=absorbance of the characteristic absorption band of the starting material at time $t_0$ (i.e., start of the reaction), and
   f) terminating the production or modification reaction when the desired degree of reaction or modification has been reached.

2. The process of claim 1 in which the reactor contents into which the IR-ATR probe is inserted have a viscosity of from 10 to 1000 Pas.

3. The process of claim 1 in which the reactor contents into which the IR-ATR probe is inserted have a viscosity of from 10 to 200 Pas.

4. The process of claim 1 in which the IR-ATR measurements are made at time intervals of from 1 second to 1 hour.

5. A process for the controlled modification of nitrile rubbers comprising
   a) determining the characteristic IR absorption band of the nitrile rubber,
   b) determining the characteristic IR absorption band of the modified nitrile rubber,
   c) immersing a probe capable of measuring IR-ATR absorption into an agitated reactor the contents of which have a viscosity of from 1 to 50 Pas and a velocity of from 0.1 to 10 m/sec at the probe location,
   d) measuring IR-ATR absorption of the reactor contents directly at time intervals of from 10 seconds to 20 minutes during the modification reaction,
   e) calculating the degree of modification of the nitrile rubber from the absorption bands generated in d) using the following equation:

$$M(t) = 100 - \frac{A(t)}{A(t_0)} \cdot 100(\%)$$

in which
M(t)=degree of modification,
A(t)=absorbance of characteristic band of the nitrile rubber starting material at time t, and
$A(t_0)$=extinction of characteristic band of the nitrile rubber starting material at time $t_0$ and
   f) terminating the modification reaction when the desired degree of modification has been reached.

\* \* \* \* \*